(12) United States Patent
Butz et al.

(10) Patent No.: US 10,694,993 B2
(45) Date of Patent: Jun. 30, 2020

(54) METHODS OF DETERMINING ENERGY BALANCE USING BREATH CARBON ISOTOPE RATIOS

(71) Applicants: Wisconsin Alumni Research Foundation, Madison, WI (US); The United States of America, as represented by the Secretary of Agriculture, Washington, DC (US)

(72) Inventors: Daniel Elmer Butz, Madison, WI (US); Leah D. Whigham, El Paso, TX (US); Mark E. Cook, Madison, WI (US); Warren Paul Porter, Fitchburg, WI (US); David H. Abbott, Madison, WI (US); Dale A. Schoeller, Belleville, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 174 days.

(21) Appl. No.: 16/058,059

(22) Filed: Aug. 8, 2018

(65) Prior Publication Data

US 2018/0353124 A1 Dec. 13, 2018

Related U.S. Application Data

(63) Continuation of application No. 14/152,316, filed on Jan. 10, 2014, now abandoned.

(51) Int. Cl.
| | | |
|---|---|---|
| A61B 5/00 | (2006.01) |
| A61K 49/00 | (2006.01) |
| A61D 99/00 | (2006.01) |
| G01N 33/497 | (2006.01) |
| G01N 33/00 | (2006.01) |
| A61B 5/08 | (2006.01) |
| A61K 41/00 | (2020.01) |

(52) U.S. Cl.
CPC .............. *A61B 5/486* (2013.01); *A61B 5/082* (2013.01); *A61B 5/4866* (2013.01); *A61D 99/00* (2013.01);
(Continued)

(58) Field of Classification Search
None
See application file for complete search history.

(56) References Cited

U.S. PATENT DOCUMENTS 4,298,347 A * 11/1981 Walsh .................. A61B 5/0813
436/133
5,912,178 A * 6/1999 Porter ...................... C12Q 1/00
436/55

(Continued)

OTHER PUBLICATIONS

Gautier et al., Changes in breath 13CO2/12C02 during exercise of different intensities, 1996, J. Appl. Physiol. 81(3): 1096-1102. (Year: 1996).*

(Continued)

*Primary Examiner* — Michael R Bloch
(74) *Attorney, Agent, or Firm* — Cantor Colburn LLP (57) ABSTRACT

Described herein are methods of determining energy balance in individuals such as exercising individuals, individuals consuming a $^{13}$C-enriched test composition and individuals consuming a fixed diet with a known $\delta^{13}$C. The $\delta^{13}$C pre- and post-exercise, or pre- and post-consumption of the test beverage or fixed diet indicate whether the individual is in neutral or positive energy balance, or in energy deficit. The methods are particularly useful for individuals participating in weight management programs, and individuals under the care of health care professionals.

10 Claims, 3 Drawing Sheets

(52) U.S. Cl.
CPC ...... *A61K 41/0028* (2013.01); *A61K 49/0004* (2013.01); *G01N 33/004* (2013.01); *G01N 33/497* (2013.01)

(56) References Cited

U.S. PATENT DOCUMENTS

| | | | |
|---|---|---|---|
| 7,465,276 B2 | 12/2008 | Assadi-Porter et al. | |
| 8,435,187 B2 | 4/2013 | Assadi-Porter et al. | |
| 8,512,676 B1 | 8/2013 | Eghbalnia et al. | |
| 2004/0035611 A1* | 2/2004 | Honda | A61B 5/0537 177/25.19 |
| 2004/0117212 A1* | 6/2004 | Kong | A61B 5/0205 705/2 |
| 2006/0253045 A1* | 11/2006 | Coifman | A61B 5/0871 600/538 |
| 2007/0243974 A1* | 10/2007 | Li | A63B 24/0084 482/8 |
| 2007/0248540 A1* | 10/2007 | Hellerstein | A61K 49/0004 424/1.61 |
| 2008/0107569 A1* | 5/2008 | Stefano | A61B 5/097 422/84 |
| 2013/0288208 A1* | 10/2013 | Yamada | G09B 19/0092 434/127 |
| 2015/0196248 A1 | 7/2015 | Cook et al. | |

OTHER PUBLICATIONS

Barstow et al., Changes in breath 13CO2/12CO2 consequent to exercise and hypoxia, 1989, J. Appl. Physiol. 66(2): 936-942 (Year: 1989).*

Barstow et al.; "Changes in Breath 12CO2/12CO2 Consequent to Exercise and Hypoxia"; J. Appl. Physiol.; 66(2); pp. 936-942; (1989).

Boriosi et al.; "Changes in Breath Carbon Isotope Composition as a Potential Biomarker of Inflammatory Acute Phase Response in Mechanically Ventilated Pediatric Patients", TJ. Anal. At. Spectrom.; advance publication; http://pubs.rsc.org/en/jounals/arti; (2013).

Butz et al.; "Changes in the Natural Abundance of 13CO2/12CO2 in Breath due to Lipopolysacchride-induced Acute Phase Response"; Rapid Communications in Mass Spectrometry; 23; pp. 3729-3735; (2009).

Butz et al.; "Immediate Biofeedback for Energy Balance Via Expired Breath $\delta 12$ CO2*", Conf Proc IEEE Eng Med Biol Soc., pp. 8205-8208; (2015).

Butz et al.; The Emerging Role of Carbon Isotope Ratio Determination in Health Research and Medical Diagnostics; J. Anal. At. Spectrom; advance article; http://pubs.rsc.org/en/journals/articlecollectionlanding?sercode=ja&themeid=329efaa4-86bc-43b1-9eb0; (2014).

Butz et al.; "The Expired Breath Carbon Delta Value is a Marker for the Onset of Sepsis in a Swine Model"; J. Anal. At. Spectrom; Advance article; http://pubs.rsc.org/en/journals/articlecollectionlanding?sercode=ja&themeid=329efaa4-86bc-43b1-9eb0-f04ecfd; (2014).

Gautier et al.; "Changes in Breath 12CO2/12CO2 During Exercise of Different Intensities"; J. Appl. Physiol.; 81(3); pp. 1096-1102; (1996).

Whigham et al.; Oral Presentation; "Changes in Energy Balance and Substrate Utilization Identified from Breath Carbon Stable Isotope Ratios"; Presented at the 30th Annual Meeting of the Obesity Society of America, Sep. 20-24, 2012, San Antonio Texas, submitted Mar. 12, 2012.

* cited by examiner

METHODS OF DETERMINING ENERGY BALANCE USING BREATH CARBON ISOTOPE RATIOS

CROSS-REFERENCE TO RELATED APPLICATIONS

This application is a continuation of U.S. application Ser. No. 14/152,316 filed on Jan. 10, 2014, which is incorporated herein by reference in its entirety.

FIELD OF THE DISCLOSURE

The present disclosure is related to methods of use of breath carbon isotope ratios to obtain non-invasive personalized biofeedback and a medical health indication of the caloric needs of a patient.

BACKGROUND

Innovative advances in breath analysis provide opportunities for non-invasive personalized biofeedback for medical conditions. Cavity ring-down spectroscopy (CRDS), in particular, provides a highly accurate, precise, and rapid table-top methodology for measuring stable isotopes in exhaled breath. Breath isotopes provide information about metabolic processes within the body. One such application is the decrease in $^{13}C$ natural abundance in breath, a biomarker for the catabolic state.

A noninvasive, non-doping, rapid stable isotope method to discern the onset of the catabolic state by detecting isotopic changes in the exhaled $CO_2$ in breath was described in U.S. Pat. No. 5,912,178 (the '178 patent). The relative health of an organism was determined by comparing the sampled ratio ($C^{13}:C^{12}$) to a baseline ratio in the organism by testing breath samples in a mass spectrometer, for example. The methods disclosed in the '178 patent allow for a non-invasive determination of net catabolic processes of organisms experiencing altered organ function or a deficit in nutrient intake.

Similarly, in U.S. Pat. No. 7,465,276 (the '276 patent), the relative amounts of first and second breath isotopes are measured over time to determine if an organism is experiencing a viral or bacterial infection. Advantages of the method of the '276 patent are that breath samples from an isotopically unenriched organism can be monitored for changes in isotope ratios over time to determine if the organism is experiencing a bacterial or viral infection. A baseline measurement from the healthy subject is preferred so that changes from the baseline can be measured that are indicative of infection. Measurements can be obtained over several hours or even several days so that the change in isotope ratio from the baseline ratio can be determined.

In addition, U.S. Pat. No. 8,512,676 describes the use of oscillation modes in breath isotope ratio data to identify an "unhealthy" state in an organism. Changes in the frequency and/or amplitude of the oscillation modes can be correlated with the health of an individual. Advantageously, advances in cavity ringdown spectrometry allow for the continuous collection of breath isotope data which permits the identification of oscillatory patterns within the breath isotope data. The identified oscillation modes are particularly useful in determining the transition from a healthy to an infected state in an organism within the short-term infection period, e.g., 30 minutes to 2 hours.

While previous methods using determination of breath isotope ratios are well-suited for their intended purpose, it is desirable to find additional uses for breath isotope ratios as a non-invasive biofeedback tool.

BRIEF SUMMARY

In one aspect, a method of determining energy balance in an exercising individual comprises obtaining a pre-exercise breath sample from the individual, exercising the individual for a period of time, obtaining a post-exercise breath sample from the individual, and determining a $\delta^{13}C$ of the pre-exercise breath sample and a $\delta^{13}C$ of the post-exercise breath sample. An increased post-exercise $\delta^{13}C$ compared to the pre-exercise $\delta^{13}C$ indicates that the individual is at neutral or positive energy balance, and a substantially constant post-exercise $\delta^{13}C$ compared to the pre-exercise $\delta^{13}C$ indicates that the individual is in energy deficit.

In another aspect, a method of determining energy balance in an individual comprises obtaining a pre-test breath sample from the individual, administering a $^{13}C$-enriched test composition to the subject, wherein a $\delta^{13}C$ of the $^{13}C$-enriched test composition is increased relative to a $\delta^{13}C$ of the pre-test breath sample, obtaining a post-test breath sample from the individual within 0.25 to 6 hours of administering the $^{13}C$-enriched test composition, and determining the $\delta^{13}C$ of the pre-test breath sample and a $\delta^{13}C$ of the post-test breath sample. An increased post-test $\delta^{13}C$ compared to the pre-test $\delta^{13}C$ indicates that the individual is in neutral or positive energy balance, and a substantially constant post-test $\delta^{13}C$ compared to the pre-test $\delta^{13}C$ indicates that the individual is in energy deficit.

In yet another aspect, a method of determining energy balance in an individual consuming a fixed diet with a known $\delta^{13}C$ comprises the individual consuming the fixed diet with known $\delta^{13}C$ on a first day, wherein the $\delta^{13}C$ of the fixed diet is increased relative to a $\delta^{13}C$ of the individual's breath, and wherein the fixed diet includes at least a first meal and a second meal, obtaining a first day breath sample from the individual, obtaining a second day breath sample from the individual, wherein the first day breath sample and the second day breath sample are taken at approximately the same time of day and about 24 hours apart, and determining a first day breath sample $\delta^{13}C$ and a second day breath sample $\delta^{13}C$. An increased second day $\delta^{13}C$ compared to the first day $\delta^{13}C$ indicates that the individual is in neutral or positive energy balance, and a substantially constant second day $\delta^{13}C$ compared to the first day $\delta^{13}C$ indicates that the individual is in energy deficit.

The above-described and other features will be appreciated and understood by those skilled in the art from the following detailed description, drawings, and appended claims.

DETAILED DESCRIPTION

It has been discovered that breath carbon isotope ratio (i.e., $^{13}CO_2/^{12}CO_2$; $\delta^{13}C$ value) responds differently to exercise in people depending on if they are in energy balance (i.e., consuming a weight-maintenance diet, WM) compared to if they are in energy deficit (ED, consuming fewer calories than their body needs). There is no current method for monitoring energy deficit, per se. The state of the art method to determine if a person is in WM or ED is simply body weight over time. However, body weight is not an accurate indicator of energy balance over short periods of time (it is best used 1-2 times per week) because many factors influence body weight in the short-term. Breath $\delta^{13}C$ analysis is useful for detecting changes in energy balance in much shorter time (e.g., within a day). This information would likely have a greater impact on changing a person's behavior because the feedback will be more closely linked in time with the behavior(s) impacting the energy balance.

In one aspect, a method of determining energy balance in an exercising individual, comprises obtaining a pre-exercise breath sample from the individual, exercising the individual for a period of time, obtaining a post-exercise breath sample from the individual, and determining a $\delta^{13}C$ of the pre-exercise breath sample and a $\delta^{13}C$ of the post-exercise breath sample, wherein an increased post-exercise $\delta^{13}C$ compared to the pre-exercise $\delta^{13}C$ indicates that the individual is at neutral or positive energy balance, and a substantially constant post-exercise $\delta^{13}C$ compared to the pre-exercise $\delta^{13}C$ indicates that the individual is in energy deficit.

As used herein, the breath delta value ($\delta^{13}C$) is calculated using the following formula with Pee Dee Belemnite (PDB) as the reference standard.

$$\delta^{13}C = \frac{(^{13}C/^{12}C \text{ sample} - ^{13}C/^{12}C \text{ PDB})}{^{13}C/^{12}C \text{ PDB}} \times 1000 \quad \text{Data are expressed as delta values in parts per mil}$$

(‰):

The standard isotope ratio of PDB is 0.0112372. A positive $\delta^{13}C$ occurs when the measured isotope ratio is higher relative to PDB, while a negative $\delta^{13}C$ occurs when the measured isotope ratio is lower relative to PDB. Since PDB contains the heaviest known naturally occurring $^{13}C/^{12}C$ ratio, all measurements of the natural abundance of carbon isotopes are negative.

In one aspect, breath samples, such as the pre-exercise breath sample and the post-exercise breath sample, are collected in sample bags such as 1 L Tedlar or metal foil bags. Breath samples can be directly collected into an instrument designed for such collection. In one embodiment, the post-exercise sample is taken within 1 minute to 5 hours after completion of exercise, specifically 5 minutes to 4 hours after completion of exercise, and more specifically 10 minutes to 2 hours after completion of exercise.

In one embodiment, relative isotope measurements are made using cavity ringdown spectroscopy (CRDS). CRDS uses infrared laser absorption to measure the concentrations of $^{13}CO_2$ and $^{12}CO_2$ carbon signals, and reports precise total $CO_2$ levels as well as the $^{13}CO_2/^{12}CO_2$ ratio. An exemplary instrument is a Picarro G2101-i Isotopic $CO_2$ analyzer. Other methods to measure breath $\delta^{13}C$ include isotope mass spectrometry.

In one aspect, the exercise intensity is aerobic exercise. Aerobic exercise is sustained exercise that stimulates and strengthens the heart and lungs, improving the body's oxygen utilization. Examples of aerobic exercise include jogging, running, brisk walking, rowing, swimming, cycling, and the like. Aerobic exercise causes a temporary increase in respiration and heart rate. The duration of the exercise is, for example, less than or equal to one hour, although longer times are within the scope of the present disclosure.

In one aspect, the individual is a participant in a weight-loss program consuming an energy-restricted diet. The methods of the present disclosure can be used to provide people who are attempting to lose weight with an objective assessment of their energy balance. Although the market for weight loss products and services is very large, there exists a need for improved methods for monitoring energy deficit. While the accepted method to determine if a person is in weight maintenance (WM) or energy deficit (ED, weight loss) is simply body weight over time, body weight is not an accurate indicator of energy balance over short periods of time. Shorter term, more reliable methods of monitoring energy deficit would provide increased feedback to persons attempting to lose weight, maintain their current weight, or gain weight, thereby encouraging people to continue with a weight-loss or weight-gain program.

For example, when an individual is trying to lose weight, the individual typically attempts to maintain a negative energy balance by consuming fewer calories than his/her body needs. To test if this goal is being met, the individual would have a breath sample analyzed before and after exercising. If the breath $\delta^{13}C$ does not change after exercise, the individual has confirmation of an energy deficit. If the breath $\delta^{13}C$ increases after exercise, the individual knows fewer calories should be consumed to achieve energy deficit and weight loss.

Diet is defined as the amount and type of food and drink consumed by an individual on a daily basis. As used herein, an energy-restricted diet is a diet that provides less energy intake than expenditure. In general, the purpose of an energy-restricted diet is weight loss and/or improvement in body composition. Energy-restricted diets include calorie-restricted diets (hypocaloric diets) as well as composition-restricted diets such as diets restricted in sugars and carbohydrates. In one aspect, when the individual is in weight maintenance according to the breath $\delta^{13}C$ values, the method further comprises recommending a reduction in calorie intake or an increase in exercise.

As used herein, an energy-excess diet is a diet that provides more energy intake than expenditure. For example, if a hypercaloric diet is consumed optionally in combination with resistance training, both fat mass and muscle mass increases can occur. In one embodiment the individual is an individual in need of body mass increase, wherein the individual consumes an energy-excess diet. Such individuals include athletes such as body builders, contact sports athletes (e.g., football, wrestling, boxing, hockey, basketball, and rugby) and endurance athletes. This method is also useful for subjects with eating disorders such as anorexia nervosa. In one aspect, when the individual is in energy deficit according to the breath $\delta^{13}C$ values, the method further comprises recommending an increase in calorie intake or a decrease in exercise.

Patients with eating disorders such as anorexia nervosa, for example, are often encouraged to eat enough calories to maintain or gain weight. The simple exercise test disclosed herein can confirm that the patient is successfully consuming enough calories. Such information is critical because eating disorder patients are often very resistant to eating and need to be coaxed into consuming adequate calories. Eating disorder patients also typically like and want to exercise, so performing a test based on exercise would likely be accepted by the patient.

In one embodiment, the increased post-exercise $\delta^{13}C$ is greater than or equal to 0.7% during neutral or positive energy balance, and the substantially constant post-exercise $\delta^{13}C$ is increased less than 0.7% in energy deficit.

The method of determining energy balance in an exercising individual can be used, for example, in health clubs or health centers that promote weight loss to determine if clients are successfully maintaining a negative or positive energy balance. The health club can offer the test described herein to people who come to the facility to exercise, providing a value-added service for membership to the facility and increasing motivation to use the facility and to regularly exercise.

In another embodiment, a method of determining energy balance in an individual comprises obtaining a pre-test breath sample from the individual, administering a $^{13}C$-enriched test composition to the subject, wherein a $\delta^{13}C$ of the $^{13}C$-enriched test composition is increased relative to a $\delta^{13}C$ of the pre-test breath sample, obtaining a post-test breath sample from the individual within 0.25 to 6 hours of administering the $^{13}C$-enriched test composition, and determining a $\delta^{13}C$ of the pre-test breath sample and a $\delta^{13}C$ of the post-test breath sample, wherein an increased post-test $\delta^{13}C$ compared to the pre-test $\delta^{13}C$ indicates that the individual is in neutral or positive energy balance, and a substantially constant post-test $\delta^{13}C$ compared to the pre-test $\delta^{13}C$ indicates that the individual is in energy deficit.

In one embodiment, the increased post-test $\delta^{13}C$ is greater than or equal to 0.7% during neutral or positive energy balance, and the substantially constant post-test $\delta^{13}C$ is increased less than 0.7% in energy deficit.

In one embodiment, the $\delta^{13}C$ of the $^{13}C$-enriched test composition is known. For example, the $\delta^{13}C$ of the $^{13}C$-enriched test composition can be calculated from known $\delta^{13}C$ values of the components of the diet. In another aspect, diet can be analyzed by isotope ratio mass spectroscopy as explained in the Examples herein. In one aspect, the $^{13}C$-enriched test composition is rich in carbohydrates, such as a liquid sweetened with cane sugar, corn sugar, or corn oil. For example, the $\delta^{13}C$ of cane sugar is −12.9% and $\delta^{13}C$ of corn syrup is −11.8%. In one embodiment, the $^{13}C$-enriched test composition is orally administered.

In one aspect, the $\delta^{13}C$ of a mixed meal is calculated using the $\delta^{13}C$ of the individual food components of the meal. The $\delta^{13}C$ of a food can be calculated by freeze-drying the food, weighing the dried food, and analyzing the dried food using, for example, an isotope ratio mass spectrometer as described herein. In one aspect, the $\delta^{13}C$ is weighted such that the contribution of individual foods to the isotopic signature of a meal is relative to the caloric contribution of the food item to the total caloric contribution of the food item to the total caloric content of the meal.

In one embodiment, the post-test breath sample from the individual is obtained within 0.25 to 6 hours of administering the $^{13}C$-enriched test composition, specifically within 1 to 6 hours, and more specifically within 4 to 6 hours.

In one embodiment, the individual is a patient under the care of health personnel such as an individual in terminal care, an individual receiving intragastric or intraparenteral nutrition, an individual undergoing cancer treatment, an individual in elder care, an individual with AIDS, an individual in convalescence following trauma, surgery or burn, or an individual with an eating disorder. The methods disclosed herein are particularly useful to heath care professionals to assess whether a patient is in energy deficit or balance, that is, to determine if the patient is consuming enough calories.

Cancer patients and the elderly often have appetite changes and/or swallowing difficulties that make adequate caloric consumption a challenge. If, for example, a cancer patient is not feeling hungry due to effects of chemotherapy or the cachectic response (muscle wasting and lack of appetite due to immune response) typical of cancer and some other diseases, the test disclosed herein could be used to monitor such patients and keep encouraging them to eat until they achieve an energy balance on a daily basis.

In another embodiment, the individual is a patient in an intensive care unit or a neonate in a neonatal care unit. Such patients are often subject to intragastric feeding or total intraparenteral nutrition which present challenges for physicians to determine if the patient is obtaining adequate nutrition. Not only do intragastric and intraparenteral feeding present difficulties in accurately calculating energy needs, but the underlying cause of the illness can make calculating energy needs difficult. For example, burn patients require additional calories depending on the burn severity, but calculating the specific needs of a specific patient is difficult. By subjecting the patient to a challenge with a $^{13}C$-enriched test composition and obtaining breath samples, the physician can noninvasively determine the energy balance in the patient. If it is determined that the patient is in neutral or positive energy balance, the feeding rate can be maintained. However, if the patient is in negative energy balance, the physician can increase the rate of gastric and/or parenteral feeding to provide a neutral or positive energy balance.

The methods described herein provide advantages over prior art methods such as the metabolic cart. A metabolic cart is an electronic medical tool to measure the body's metabolism through oxygen consumption and carbon dioxide production when the body is at rest using indirect calorimetry. In general, the components of the device (a computer system, monitor, and breathing tubes) are housed on mobile push cart. The consumption of oxygen for the body and the production of carbon dioxide are measured to calculate the REE, or resting energy expenditure. The metabolic cart measures the calories burned by the individual. However, the metabolic cart method has significant limitations including: (1) cart sampling often requires at least 30 minutes of breath sampling per session; (2) the data obtained from cart sampling can be unreliable if the patient is disturbed during sampling; and (3) the equations used to calculate the energy requirements using the metabolic cart are often based on healthy individuals and do not account for the altered metabolic needs during disease, injury and recovery from illness. The methods of the present disclosure, in contrast, allow for the measurement of energy balance rather than energy expenditure (from which energy balance is calculated based on assumptions about the individual's health status). The present disclosure does not rely on the health status of the individual in order to determine energy balance. In addition, in order to obtain data with a metabolic cart, the patient must lie still with a mask over their face or a hood over their head for at least 20 minutes, generally 30-40 minutes, which may not be practical for ICU/NICU patients (interfering with other tubing/equipment, getting infants to lie still). Also, the metabolic cart method provides resting energy expenditure, not total energy needs, so the physician still has to guess as to the additional calories needed when the patient is not at rest. This value could vary significantly from person to person, particularly in athletes, eating disorder patients, and people trying to lose weight, in addition to day to day variance in individuals. Measuring energy balance factors in the individual's needs and the day to day variance.

In another aspect, the individual is a subject in a human study in which dietary compliance is determined or monitored. For example, researchers are trying to find new ways to reduce obesity. In some of these studies researchers are investigating the effects of new diet or pharmaceutical agents to reduce energy consumption. The use of the breath $\delta^{13}C$ would allow the researchers to quickly assess the affects of the intervention in reducing caloric need relative to intake. In addition, subjects in a weight loss study might consume food other than that which has been provided to them. The method disclosed herein would allow monitoring of dietary compliance in weight loss studies in free-living subjects which is desirable to researchers because ultimately weight loss methods are for use by free-living people.

A method of determining energy balance in an individual consuming a fixed diet with a known $\delta^{13}C$ comprises the individual consuming the fixed diet with known $\delta^{13}C$ on a first day, wherein the $\delta^{13}C$ of the fixed diet is enriched relative to a $\delta^{13}C$ of the individual's breath, and wherein the fixed diet includes at least a first meal and a second meal, obtaining a first day breath sample from the individual, obtaining a second day breath sample from the individual, wherein the first day breath sample and the second day breath sample are taken at approximately the same time of day and about 24 hours apart, and determining a first day breath sample $\delta^{13}C$ and a second day breath sample $\delta^{13}C$, wherein an increased second day $\delta^{13}C$ compared to the first day $\delta^{13}C$ indicates that the individual is in neutral or positive energy balance and a substantially constant second day $\delta^{13}C$ compared to the first day $\delta^{13}C$ indicates that the individual is in energy deficit.

In one embodiment, the fixed diet is administered over a period of 2 days to 7 days or longer, and a breath sample is taken at approximately the same time each day over about 24 hour intervals. This method allows energy balance to be determined over an extended period of time. The breath sample can be taken pre-meal (e.g., pre-breakfast) or post-meal (e.g., post-breakfast), as long as the sample is taken under the same conditions each day.

In one embodiment, the increased second day $\delta^{13}C$ is greater than or equal to 0.7% during neutral or positive energy balance, and the substantially constant second day $\delta^{13}C$ is increased less than 0.7% in energy deficit.

In one embodiment, the individual is an agricultural animal such as, for example, cattle, swine, horses, sheep, chickens, ducks, turkeys, pheasants, and fish. In another embodiment, the individual is a domesticated pet such as a dog or cat. The method of determining energy balance in animals is particularly advantageous because it is noninvasive and administering fixed diets to animals is routinely practiced.

In one embodiment, the individual is a human and the increased second day $\delta^{13}C$, when compared to the first day $\delta^{13}C$ is at least 0.7% during neutral or positive energy balance, and the substantially constant $\delta^{13}C$ from the first day to the second day is less than 0.7% in energy deficit.

In another embodiment, the individual is a human individual in terminal care, an individual receiving intragastric or intraparenteral nutrition, an individual undergoing cancer treatment, an individual in elder care, an individual with AIDS, an individual in convalescence following trauma, surgery or burn, or an individual with an eating disorder. In another embodiment, the individual is a subject in a human study in which dietary compliance is determined or monitored. In yet another embodiment, the individual is a human individual adhering to a weight loss diet regimen. As used herein, a weight-loss diet regimen is a calorie-restricted diet.

The invention is further illustrated by the following non-limiting examples.

EXAMPLES

Example 1: Use of Breath Isotopes to Monitor Compliance to an Energy Restricted Diet in Humans Methods This study was approved by the University of Wisconsin-Madison Institutional Review Board. All volunteers provided written informed consent. Healthy volunteers (n=5) 18 years and older with no metabolic or digestive problems or food allergies were recruited for the study. Volunteers consumed three study meals per day for 7 days. Volunteers decided what time to consume meals but were instructed to follow similar meal times throughout the 7 days. Meals on days 1-6 contained approximately 40% fewer kcal than required for weight maintenance and approximately 50% excess kcal on day 7. On the morning of day 8, volunteers consumed a breakfast comparable to days 1-6. Total energy requirements were estimated using calculations for resting energy expenditure (REE) based on age, height, weight, and sex known in the prior art with a physical activity level of 1.65. The following equations used were:

$$REE(males)=10\times weight(kg)+6.25\times height(cm)-5\times age(y)+5$$

$$REE(females)=10\times weight(kg)+6.25\times height(cm)-5\times age(y)-161$$

Volunteers collected breath in 1-L air sampling bags (SKC Inc., Eighty Four, Pa.) just prior to and 1 hour and 2 hour following each meal. Breath was analyzed within 48 hours using a CRDS (Picarro, Sunnyvale, Calif., USA). Diet was analyzed by isotope ratio mass spectroscopy. Food items were homogenized, freeze dried, and powdered. Approximately 1 mg of each food item was added to tin capsules and inserted into the elemental analyzer where it was oxidized and the $^{13}C$ abundance was analyzed using a Delta V Isotope Ratio mass spectrometer coupled to the elemental analyzer via a Finnigan Conflo III universal interface (Thermo Electron, Bremen, Germany). The $^{13}C$ abundance for the meal was calculated by weighing the $^{13}C$ abundance for each food item in proportion to its fractional contribution to the total carbon of the meal. The isotopic abundance of $^{13}C$ was expressed as a relative change in the ratio of $^{13}C/^{12}C$ in a sample compared to a Pee Dee Belemnite as described herein.

This notation simply translated is ten times the percent difference in the isotope ratio relative to the standard.

Statistical Analyses: Data are presented as mean±standard deviation (SD). Repeated measures analysis of variance (ANOVA) was used to test for changes across time in pre-breakfast and in day 7 breath $\delta^{13}C$. Dunnett's contrasts were used for post-hoc comparisons; pre-breakfast breath $\delta^{13}C$ on days 2-7 were compared to day 1; and postprandial day 7 time points were compared to pre-breakfast day 7. SAS V9.2 (SAS Institute, Inc., Cary N.C.) was used for all statistical analyses. P<0.05 was considered significant.

Results

Figure 1:
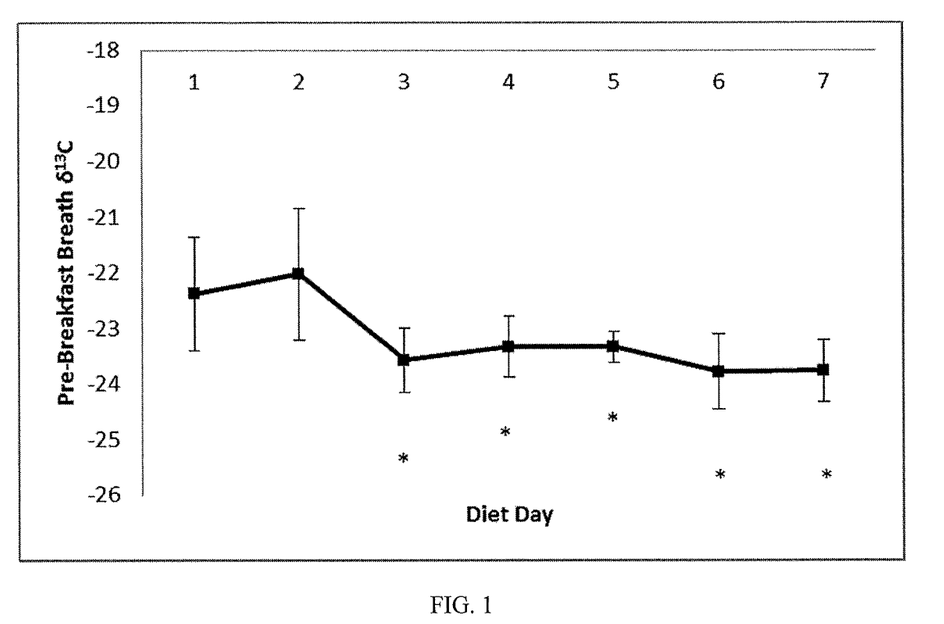
FIG. 1 shows breath $\delta^{13}C$ values of pre-breakfast breath across 7 days on a hypocaloric diet. *Significantly different from pre-breakfast day 1, p<0.05 by Dunnett's comparisons.
Figure 2:
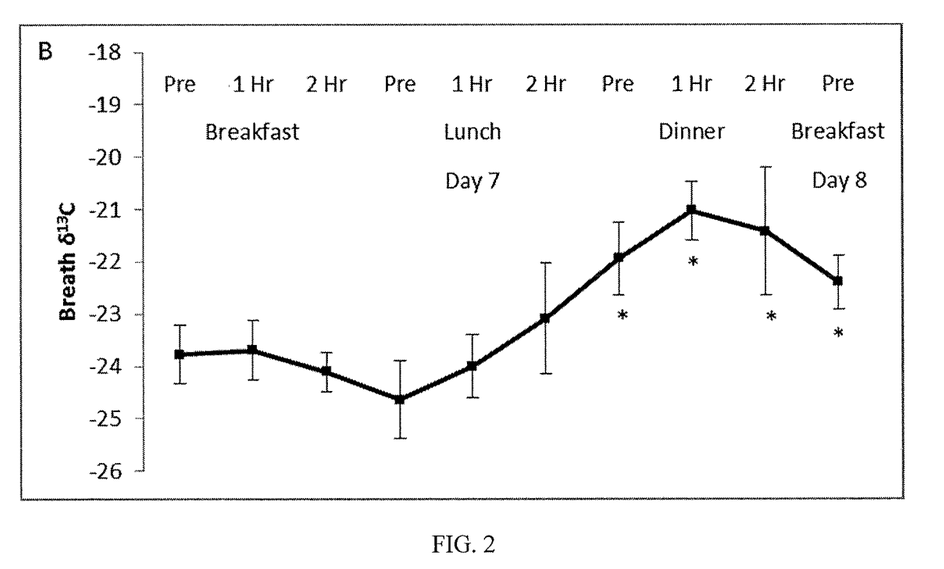
FIG. 2 shows breath $\delta^{13}C$ values on day 7 during a hypercaloric diet (breakfast, lunch, and dinner). Although excess caloric intake started at breakfast (620 kcal vs. 420 kcal for breakfast on days 1-6), subjects most likely did not reach positive energy balance until lunch was consumed (1500 kcal). *Significantly different from pre-breakfast day 7, p<0.05 by Dunnett's comparisons.
Figure 3:
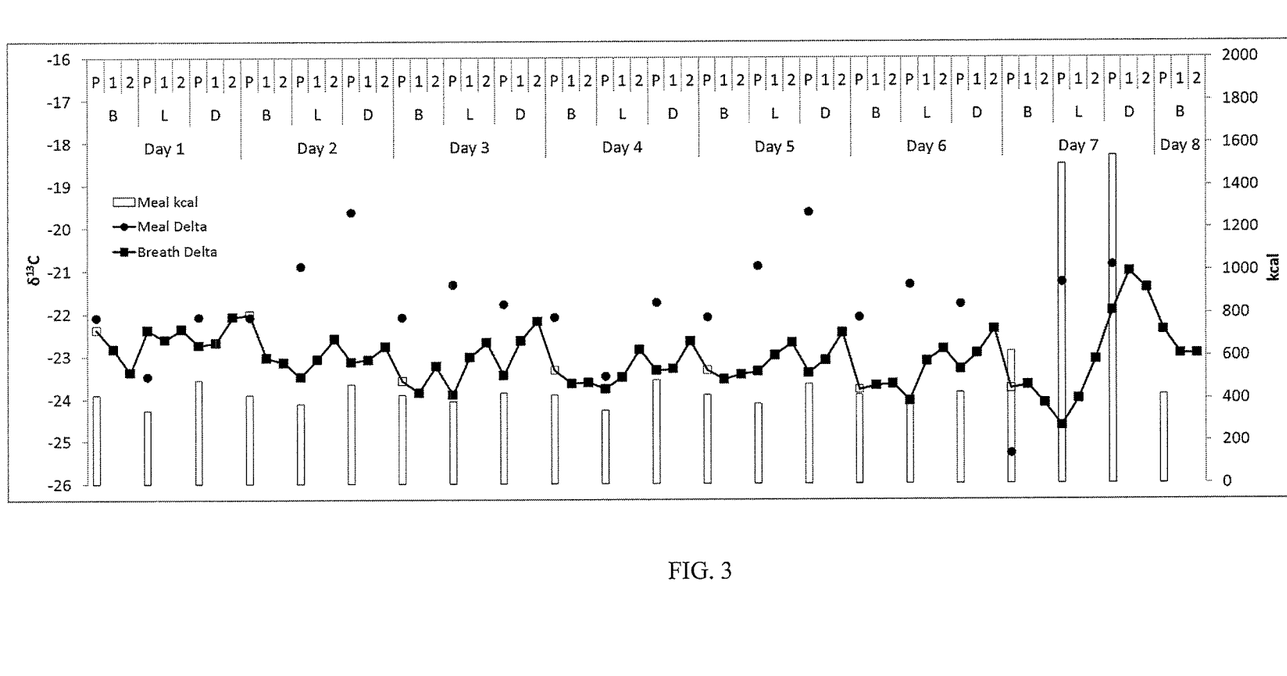
FIG. 3 shows breath $\delta^{13}C$ values (squares) related to meal $\delta^{13}C$ values (circles) and meal energy content (open bars). Open squares represent pre-breakfast breath $\delta^{13}C$ values shown in FIG. 1.

Non-obese volunteers (n=5; 2 female) were 48.0±12.1 years of age with a BMI of 25.2±0.8 kg/m². Estimated energy requirements for these subjects were calculated to be 2550-2770 kcal (10,673-11,595 kJ). Consumption of the energy restricted diet decreased the pre-breakfast breath $\delta^{13}C$ from −22.4±1.0% on day 1 to −23.6±0.6% on day 3 (P<0.007, FIG. 1). The more negative, pre-breakfast breath $\delta^{13}C$ were maintained for the remaining period of energy restriction (range of −23.3 to −23.8%, P<0.05 compared to day 1), including the day 7 pre-breakfast breath $\delta^{13}C$ of −23.8±0.6%. By pre-dinner on day 7 (first day of hypercaloric feeding), breath $\delta^{13}C$ increased (P=0.002) to −21.9±0.7 and remained elevated 2 hours after dinner (FIG. 2). FIG. 3 shows breath $\delta^{13}C$ across all time points along with meal $\delta^{13}C$ and energy level of each meal. Breakfast, lunch, and dinner $\delta^{13}C$ means on days 1-6 were −22.1, −21.9, and −21.1%, respectively, compared to meal $\delta^{13}C$ day 7 of −25.3, −21.3, and −20.9, respectively.

DISCUSSION

This study was designed to demonstrate proof of concept for a novel use of naturally occurring breath stable isotope ratios of carbon to monitor compliance to an energy restricted diet in humans. The technique provides a biofeedback tool for individuals attempting to lose weight by consuming an energy restricted diet. Consumption of an energy restricted diet resulted in a decrease in pre-breakfast breath $\delta^{13}C$ after 3 days. Throughout the remainder of the energy restricted phase of the diet, breath $\delta^{13}C$ values remained relatively low despite transient rises in meal $\delta^{13}C$ values (FIG. 3), potentially indicating that breath was more representative of the substrate being utilized (i.e., stored fat) than the diet consumed during energy restriction.

On day 7, breath $\delta^{13}C$ became isotopically heavier by dinner, despite meal $\delta^{13}C$ values differing little from meals consumed during days 1-6. The breakfast meal on day 7, while higher in energy than breakfast on days 1-6 (620 vs. 420 kcal or 2594 vs. 1757 kJ, respectively), was likely not sufficiently caloric to shift individuals from negative to positive energy balance, especially following an overnight fast in a person consuming an energy restricted diet for the previous 6 days. Consumption of a subsequent 1500 kcal (6276 kJ) lunch, however, appeared to shift subjects into positive energy balance, as indicated by elevated breath $\delta^{13}C$ by pre-dinner. The breath $\delta^{13}C$ remained elevated through pre-breakfast the following day (day 8).

The ability to monitor compliance with an energy restricted diet has value for investigators from a research standpoint and subjects or patients from a motivational standpoint. Current methods of monitoring compliance to prescribed dietary guidelines for weight loss include monitoring changes in weight and body composition and recording dietary intake. Tracking of weight and body composition allows for feedback on a weekly basis at best, but is not sensitive enough for daily feedback. Monitoring food intake is a commonly used treatment technique for behavioral change, but is inaccurate. Furthermore, maintaining this technique is time-consuming so few people consistently use it long-term. Personalized daily feedback, provided by breath $\delta^{13}C$ values, could allow for immediate positive reinforcement for compliance to a negative energy balance diet or timely counseling when compliance is poor.

The design of this study was intended to emulate a real-life scenario in which an individual follows a healthy, energy restricted diet for several days, followed by a day in which attempts to control energy intake are difficult to maintain in the current food environment (e.g., donuts at a breakfast meeting, drive-through fast food meal for lunch, and high-fat pizza for dinner). Further validation under highly controlled conditions with manipulation of diet $\delta^{13}C$ and caloric level independently will help to fully test specificity, robustness, and variability of responses across time of the breath $\delta^{13}C$ method. In addition, optimization of this methodology as a weight loss aid for individuals would be significantly enhanced by development of a hand-held device capable of breath carbon isotope ratio analysis. Current cavity ring-down technology, nevertheless, offers options for center-based programs in locations such as fitness centers or the work place.

Example 2: Changes in Breath $\delta^{13}C$ in Response to Exercise

Volunteers provided informed, written consent. The study was overseen by the University of North Dakota Institutional Review Board. Volunteers resided in the Metabolic Research Unit of the USDA Grand Forks Human Nutrition Research Center. On days 1-10, live-in human volunteers consumed a weight maintenance diet and participated in a prescribed, supervised exercise episode each day. On days 11-31, the volunteers were in 40% energy deficit and continued with daily exercise. The study diet was based on a 3-day menu that was individually adjusted to caloric needs (WM or ED) for each study volunteer. Exercise episodes were conducted either during the morning (following breakfast and prior to lunch) or in the afternoon (following lunch and prior to dinner), but kept the same time of day for each individual. Breath samples were collected prior to, immediately after, and 30, 60 and 90 minutes post exercise during weight maintenance and energy deficit. Study diet menu day was the same (but different caloric levels) on comparison days (WM and ED).

Figure 4:
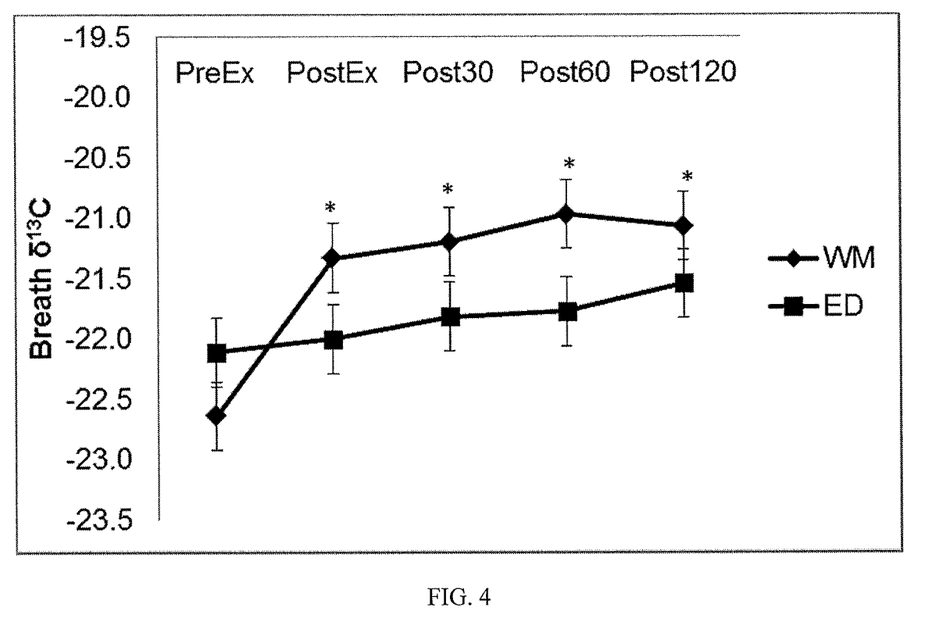
FIG. 4 shows the breath $\delta^{13}C$ values in response to exercise underweight management conditions (WM) and energy-deficit conditions (ED). *Significantly different from pre-exercise, p<0.05. PreEx=before exercise, PostEx=immediately after exercise, Post30/60/90=30/60/90 minutes after exercise.

The results are shown in FIG. 4. The breath $\delta^{13}C$ values increase in response to exercise under conditions of energy balance (WM) (P≤0.01), but do not change following exercise under conditions of energy deficit (ED). These results differ from the expected result which was an increase in breath $\delta^{13}C$ in response to exercise regardless of energy balance.

The ability to determine or monitor negative energy balance has value for investigators and health care providers. This approach could be used in research environments in which compliance to an energy restricted diet is required. Similarly, the approach could be applied in health club or clinic environments as a tool to confirm maintenance of an energy-restricted diet (e.g. individuals attempting weight loss) or conversely to confirm maintenance of a neutral or positive energy balance (e.g. patients recovering from an eating disorder such as anorexia nervosa).

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A method of administering a diet to a non-infected exercising individual or exercising the non-infected exercising individual, comprising
    obtaining a pre-exercise breath sample from the individual, wherein the individual is a participant in a weight-loss program consuming an energy-restricted diet;
    exercising the individual for a period of time, wherein exercise is aerobic exercise that causes a temporary increase in respiration and heart rate;
    obtaining a post-exercise breath sample from the individual, wherein the post-exercise breath sample is taken within 1 minute to 5 hours after completion of exercise;
    measuring a $\delta^{13}C$ of the pre-exercise breath sample and a $\delta^{13}C$ of the post-exercise breath sample using cavity ringdown spectroscopy; and
    administering a diet with a reduced calorie intake to the individual or increasing exercise in the individual when the individual is determined to be at neutral or positive energy balance post-exercise, or continuing administering the energy-restricted diet when the individual is determined to be in energy deficit post-exercise,
    wherein an increased post-exercise $\delta^{13}C$ compared to the pre-exercise $\delta^{13}C$ indicates that the individual is at neutral or positive energy balance, and a constant post-exercise $\delta^{13}C$ compared to the pre-exercise $\delta^{13}C$ indicates that the individual is in energy deficit, and
    wherein the increased post-exercise $\delta^{13}C$ is greater than or equal to 0.7% during neutral or positive energy balance, and the constant post-exercise $\delta^{13}C$ is increased less than 0.7% in energy deficit.

2. The method of claim 1, wherein the individual is determined to be at neutral or positive energy balance post-exercise, and the method comprises administering a diet with a reduced calorie intake to the individual.

3. The method of claim 1, wherein the individual is determined to be at neutral or positive energy balance post-exercise, and the method comprises increasing exercise in the individual.

4. The method of claim 1, wherein the individual is determined to be in energy deficit post-exercise, and the method comprises continuing administering the energy-restricted diet to the individual.

5. The method of claim 1, wherein the exercise is less than one hour in duration.

6. A method of administering a diet to a non-infected exercising individual or exercising the non-infected exercising individual comprising
    obtaining a pre-exercise breath sample from the individual, wherein the individual is in need of body mass increase and is consuming an energy-excess diet;
    exercising the individual for a period of time, wherein exercise is aerobic exercise that causes a temporary increase in respiration and heart rate;
    obtaining a post-exercise breath sample from the individual, wherein the post-exercise breath sample is taken within 1 minute to 5 hours after completion of exercise;
    measuring a $\delta^{13}C$ of the pre-exercise breath sample and a $\delta^{13}C$ of the post-exercise breath sample using cavity ringdown spectroscopy, and
    administering a diet with an increase in calorie intake to the individual or decreasing exercise in the individual when the individual is determined to be in energy deficit, and continuing administering the energy-excess diet when the individual is determined to be in neutral or positive energy balance post-exercise,
    wherein an increased post-exercise $\delta^{13}C$ compared to the pre-exercise $\delta^{13}C$ indicates that the individual is at neutral or positive energy balance post-exercise, and a constant post-exercise $\delta^{13}C$ compared to the pre-exercise $\delta^{13}C$ indicates that the individual is in energy deficit, and
    wherein the increased post-exercise $\delta^{13}C$ is greater than or equal to 0.7% during neutral or positive energy balance, and the constant post-exercise $\delta^{13}C$ is increased less than 0.7% in energy deficit.

7. The method of claim 6, wherein the individual is determined to be in energy deficit post-exercise, and the method comprises administering a diet with an increased calorie intake to the individual.

8. The method of claim 6, wherein the individual is determined to be in energy deficit post-exercise, and the method comprises decreasing exercise in the individual.

9. The method of claim 6, wherein the individual is determined to be in neutral or positive energy balance post-exercise, and the method comprises continuing administering the energy-excess diet to the individual.

10. The method of claim 6, wherein the exercise is less than one hour in duration.

* * * * *